US011104906B2

(12) United States Patent
Honda et al.

(10) Patent No.: US 11,104,906 B2
(45) Date of Patent: Aug. 31, 2021

(54) METHOD FOR PRODUCING COENZYME AND TRANSFORMANT SET FOR COENZYME PRODUCTION

(71) Applicant: JAPAN SCIENCE AND TECHNOLOGY AGENCY, Kawaguchi (JP)

(72) Inventors: Kohsuke Honda, Osaka (JP); Haruyuki Atomi, Kyoto (JP)

(73) Assignee: JAPAN SCIENCE AND TECHNOLOGY AGENCY, Kawaguchi (JP)

( * ) Notice: Subject to any disclaimer, the term of this patent is extended or adjusted under 35 U.S.C. 154(b) by 0 days.

(21) Appl. No.: 15/552,440

(22) PCT Filed: Feb. 19, 2016

(86) PCT No.: PCT/JP2016/054872
§ 371 (c)(1),
(2) Date: Aug. 21, 2017

(87) PCT Pub. No.: WO2016/136620
PCT Pub. Date: Sep. 1, 2016

(65) Prior Publication Data
US 2018/0044683 A1  Feb. 15, 2018

(30) Foreign Application Priority Data
Feb. 24, 2015  (JP)  ............................ JP2015-033843

(51) Int. Cl.
*C12N 15/52*  (2006.01)
*C12N 15/09*  (2006.01)
(Continued)

(52) U.S. Cl.
CPC  ............. *C12N 15/52* (2013.01); *C07H 21/04* (2013.01); *C12N 1/20* (2013.01); *C12N 5/10* (2013.01);
(Continued)

(58) Field of Classification Search
None
See application file for complete search history.

(56) References Cited

U.S. PATENT DOCUMENTS

| 4,921,786 A | 5/1990 | Takahashi et al. |
| 2011/0275135 A1 | 11/2011 | Lee et al. |
| 2013/0316364 A1 | 11/2013 | Koepke et al. |

FOREIGN PATENT DOCUMENTS

| CN | 102154339 A | 8/2011 |
| CN | 102212567 A | 10/2011 |

(Continued)

OTHER PUBLICATIONS

Thermus thermophilus DNA, complete genome, NZ_AP017920, Dec. 2019.*

(Continued)

*Primary Examiner* — Richard G Hutson
(74) *Attorney, Agent, or Firm* — Oblon, McClelland, Maier & Neustadt, L.L.P.

(57) ABSTRACT

The present invention provides a method for synthesizing NAD$^+$ or NADH in an enzyme reaction system requiring NAD$^+$ or NADH so as to supplement NAD$^+$ lost due to thermal decomposition in the enzyme reaction system, and a transformant set for coenzyme production used in the method. That is, the present invention relates to a method for producing a coenzyme including performing synthesis of NAD$^+$ or NADH in an enzyme reaction system requiring NAD$^+$ or NADH by adding one or more thermostable enzymes required for a reaction for synthesizing NAD$^+$ from (Continued)

nicotinamide, to the enzyme reaction system, and a transformant set for coenzyme production including one or more transformants into which one or more genes encoding thermostable enzymes required for a reaction for synthesizing $NAD^+$ or NADH from nicotinamide are introduced by using a non-thermostable microorganism as a host.

7 Claims, 6 Drawing Sheets

(51) Int. Cl.
  C12P 19/32    (2006.01)
  C07H 21/04    (2006.01)
  C12N 1/20     (2006.01)
  C12N 5/10     (2006.01)
  C12N 9/02     (2006.01)
  C12N 15/70    (2006.01)
(52) U.S. Cl.
  CPC .......... *C12N 9/0036* (2013.01); *C12N 15/09* (2013.01); *C12N 15/70* (2013.01); *C12P 19/32* (2013.01)

(56) References Cited

FOREIGN PATENT DOCUMENTS

| CN | 103966185 A | 8/2014 |
|---|---|---|
| JP | 63-185378 A | 7/1988 |
| JP | 2011-160778 A | 8/2011 |
| WO | WO 03/040690 A2 | 5/2003 |
| WO | WO 2006/041624 A2 | 4/2006 |

OTHER PUBLICATIONS

Thermus aquaticus Y51MC23, complete genome, NZ_CP010822, Dec. 2019.*
Partial Supplementary European Search Report dated Jun. 15, 2018 in Patent Application No. 16755366.8, 15 pages.
Jayaram, H.N. et al. "NMNAT Expression and its Relation to NAD Metabolism", Current Medicinal Chemistry, vol. 18, No. 13, XP055481991, 2011, pp. 1962-1972.
Jackson, M.D. et al. "Mechanism of Nicotinamide Inhibition and Transglycosidation by Sir2 Histone/Protein Deacetylases", The Journal of Biological Chemistry, vol. 278, No. 51, XP002457579, 2003, pp. 50985-50998.
McNeil, C.J. et al. "Thermostable Reduced Nicotinamide Adenine Dinucleotide Oxidase: Application to Amperometric Enzyme Assay", Analytical Chemistry, vol. 61, No. 1, XP055480425, Jan. 1, 1989, pp. 25-29.
Wu, X. et al. "Application of a Novel Thermostable NAD(P)H Oxidase From Hyperthermophilic Archaeon for the Regeneration of Both $NAD^+$ and $NADP^+$", Biotechnology and Bioengineering, vol. 109, No. 1, XP055481521, Jan. 2012, pp. 53-62.
Wong, C-H. et al. "Enzymatic vs. Fermentative Synthesis: Thermostable Glucose Dehydrogenase Catalyzed Regeneration of NAD(P)H for use in Enzymatic Synthesis", Journal of the American Chemical Society, vol. 107, No. 13, XP001320642, 1985, pp. 4028-4031.
International Search Report dated May 24, 2016, in PCT/JP2016/054872 filed Feb. 19, 2016.
Krutsakorn, et al., Metabolic Engineering, "In vitro production of n-butanol from glucose", 2013, vol. 20, pp. 84-91.
Ninh, et al., Biotechnology and Bioengineering, "Assembly and Multiple Gene Expression of Thermophilic Enzymes in *Escherichia coli* for In Vitro Metabolic Engineering", 2015, vol. 112, pp. 189-196.
Chenault et al., Applied Biochemistry and Biotechnology, "Regeneration of Nicotinamide cofactors for use in Organic Synthesis", 1987, vol. 14, pp. 147-197.

Yokoyama, et al., Nature Structural Biology, Structural genomics projects in Japan, 2000, vol. 7, pp. 943-945.
Gazzaniga et al., Microbial NAD Metabolism: Lessons from Comparative Genomics, Microbiology and Molecular Biology Reviews, 2009, vol. 73, No. 3, pp. 529-541.
Morimoto et al., "Alteration of the coenzyme specificity of the malic enzyme from Thermococcus kodakarensis KOD1 and its Utilization in synthetic metabolic pathway", Abstracts of the Annual Meeting of the Society for Biotechnology, Japan, 2012, vol. 64, pp. 230, 4Ha06.
Ye et al., "Synthetic metabolic engineering—a novel, simple technology for designing a chimeric metabolic pathway", Microbial Cell Factories, 2012, vol. 11, No. 120, 11 pages.
Stekhanova et al.,"Nicotinamidase from the Thermophilic Archaeon *Acidilobus saccharovorans*: Structural and Functional Characteristics", Biochemistry (Moscow), 2014, vol. 79, No. 1, pp. 54-61.
Yamaguchi et al., "Stable Ammonia-specific NAD Synthetase from Bacillus Stearothermophilus: Purification, Characterization, Gene Cloning, and Applications", Bioscience Biotechnology and Biochemistry, 2002, vol. 66, No. 10, pp. 2052-2059.
Honda et al., "In vitro metabolic engineering for the salvage synthesis of $NAD^+$", Metabolic Engineering, Available online Feb. 18, 2016, vol. 35, pp. 114-120.
Hare et al.. "Construction of $NAD^+$ salvage pathway by in vitro metabolic engineering", Annual Meeting of JSBBA Koen Yoshishu (web), Mar. 5, 2015, vol. 2015, p. 2A34P18.
Honda, "Tainetsusei Koso o Mochiita Nicotinamide Hokoso no Anteika Gijut suno Kaihatsu", Osaka University, New Technology Presentation Meetings Tojitsu Shiryo, Jul. 14, 2015, 12 total pages.
Hofmann, et al., Anal Bioanal Chem (2010), "Structure elucidation of the thermal degradation products of the nucleotide cofactors NADH and NADPH by nano-ESI-FTICR-MS and HPLC-MS", vol. 398, pp. 2803-2811.
Extended European Search Report dated Sep. 26, 2018 in Patent Application No. 16755366.8.
Svetlana Gerdes, et al., "Comparative Genomics of NAD Biosynthesis in Cyanobacteria", Journal of Bacteriology, vol. 188, XP55505928, Apr. 2006, pp. 3012-3023.
Huimin Zhao, et al., "Regeneration of cofactors for use in biocatalysts", Curren Opinion in Biotechnology, vol. 14, No. 6, XP55449232, Dec. 2003, pp. 583-589.
Werner Hummel, "Large-scale applications of NAD(P)-dependent oxidoreductases: recent developments", Trends in Biotechnology, vol. 17, No. 12, XP002237302, Dec. 1999, pp. 487-492.
Tamotsu Eguchi, et al., "Covalent linking of poly(ethyleneglycol)-bound NAD with *Thermus thermophilus* malate dehydrogenase NAD(H)-regeneration unit for a coupled second-enzyme reaction", Eur. J. Biochem., XP55506198, 1986, pp. 415-421.
Wenfang Liu, et al., "Cofactor regeneration for sustainable enzymatic biosynthesis", Biotechnology Advances, vol. 25, No. 4, XP022094827, 2007, pp. 369-384.
Susana J. Berrios-Rivera, et al., "The effect of NAPRTase Overexpression on the Total Levels of NAD, the NADH/NAD+ Ratio, and the Distribution of Metabolites in *Escherichia coli*", Metabolic Engineering, vol. 4, No. 3, XP003016934, 2002, pp. 238-247.
Bettina Siebers, et al., "Reconstruction of the Central Carbohydrate Metabolism of *Thermoproteus tenax* by Use of Genomic and Biochemical Data", Journal of Bacteriology, vol. 186, No. 7, XP55504606, Apr. 2004, pp. 2179-2194.
F. Heuser, et al., "Enhancement of the NAD(P)(H) Pool in *Escherichia coli* for Biotransformation", Engineering in Life Sciences, vol. 7, No. 4, XP55505293, Jul. 2007, pp. 343-353.
Jicai Bi, et al., "Comparative Genomics of NAD(P) Biosynthesis and Novel Antibiotic Drug Targets", Journal of Cellular Physiology, vol. 226, No. 2, XP55480606, Nov. 2010, pp. 331-340.
Liya Liang, et al., "Effects of overexpression of NAPRTase, NAMNAT, and NAD synthetase in the NAD(H) biosynthetic pathways on the NAD(H) pool, NADH/$NAD^+$ ratio, and succinic acid production with different carbon sources by metabolically engineered *Escherichia coli*", Biochemical Engineering Journal, vol. 81, XP028780571, Dec. 2013, pp. 90-96.

(56) References Cited

OTHER PUBLICATIONS

Kenji Okuda, et al., "Systematic Characterization of the ADP-Ribose Pyrophosphatase Family in the Cyanobacterium *Synechocystis* sp. Strain PCC 6803", Journal of Bacteriology, XP55506402, Jul. 2005, pp. 4984-4991.

Nian Huang, et al., "Bifunctional NMN Adenylyltransferase/ADP-Ribose Pyrophosphatase: Structure and Function in Bacterial NAD Metabolism", Structure, vol. 16, No. 2, XP022475298, Feb. 2008, pp. 196-209.

Florian Heuser, "Einfluss des NAD(H) Pools auf die Produktivität bei Ganzzellbiotransformationen", Retrieved from the Internet: URL:https://docserv.uniduesseldorf.de/servlets/DerivateServlet/Derivate-6838/Doktorarbeit%20finale%20Version%202007_11_15.pdf, XP55505685, Nov. 9, 2007, 110 pages, (with English Abstract).

Naeem Rashid, et al., "Gene Cloning and Characterization of Recombinant Ribose Phosphate Pyrophosphokinase from a Hyperthermophilic Archaeon", Journal of Fermentation and Bioengineering, vol. 83, No. 5, XP55506644, Jan. 1997, pp. 412-418.

Robson Francisco de Souza, et al., "Identification of novel components of NAD-utilizing metabolic pathways and prediction of their biochemical functions", Molecular BioSystems, vol. 8, No. 6, XP55505446, Jan. 2012, 18 pages.

Nadia Raffaelli, et al. "*Synechocystis* sp. Slr0787 protein is a novel bifunctional enzyme endowed with both nicotinamide mononucleotide adenylyltransferase and 'Nudix' hydrolase activities", Federation of European Biochemical Societies, Dec. 10, 1998, pp. 222-226.

Combined Chinese Office Action and Search Report dated May 7, 2020, in Patent Application No. 201680011483.2 (with English translation), 14 pages.

* cited by examiner

METHOD FOR PRODUCING COENZYME AND TRANSFORMANT SET FOR COENZYME PRODUCTION

TECHNICAL FIELD

The present invention relates to a method for synthesizing $NAD^+$ or NADH from decomposition products of $NAD^+$ in an enzyme reaction system requiring $NAD^+$ or NADH, and a transformant set for producing $NAD^+$ or NADH used in the method.

Priority is claimed on Japanese Patent Application No. 2015-33843, filed on Feb. 24, 2015, the content of which is incorporated herein by reference.

BACKGROUND ART

In accordance with the recent development in the technology of gene modification, a method for producing a useful organic compound by using a microorganism as a reaction system in a synthesis reaction and using a metabolic pathway that the microorganism has is being used also for industrial mass production. Furthermore, in order to synthesize an organic compound more efficiently, attempts have been made to artificially construct a synthesis pathway (artificial metabolic system) specific to a substance production by modularizing a plurality of metabolic enzymes in advance and combining the enzymes arbitrarily, without modification of a metabolic pathway of a living microorganism. It has been reported that with a method using the artificial metabolic system, for example, lactic acid, malic acid, 1-butanol, and the like can be selectively produced at high yield from glucose and glycerol (for example, refer to NPL 1).

It is possible to easily provide a metabolic enzyme modularized to be used (enzyme module) with a low cost by allowing a transformant in which a gene encoding the metabolic enzyme is introduced into a microorganism, to produce the metabolic enzyme. Among the enzymes, it is preferable to use a thermostable enzyme as the enzyme module from the viewpoint that the thermostable enzyme excels in physical and chemical stability and is suitable for industrial use. As a method for producing the thermostable enzyme by microorganisms, for example, a method in which a transformant in which a gene encoding a target thermostable enzyme is introduced into non-thermostable acid-fast bacteria is cultured to produce the thermostable enzyme in the transformant, and then the cultured transformants are heat treated, and thereby the thermostable enzyme immobilized in the dead sterilized bodies of the transformant is obtained is disclosed (for example, refer to PTL 1). In the method, because proteins derived from the acid-fast bacterium which is the host are all deactivated and only the target thermostable enzyme is immobilized in the dead sterilized bodies of the transformant in a state of maintaining the activity, there is an advantage that a side reaction caused by the enzyme derived from the host does not occur even in a case of adding the dead sterilized bodies in the reaction system as they are.

CITATION LIST

Patent Literature

[PTL 1] Japanese Unexamined Patent Application, First Publication No. 2011-160778

Non-Patent Literature

[NPL 1] Krutsakorn, et al., Metabolic Engineering, 2013, vol. 20, p. 84 to 91.

SUMMARY OF INVENTION

Technical Problem

According to the method using the artificial metabolic system, it is possible to utilize the advantage of the enzyme reaction that excels in substrate specificity and stereoselectivity of a compound and that can be synthesized a target organic compound under relatively mild conditions, and to more efficiently produce an organic compound which was difficult to produce through organic synthesis. However, the method is poor in terms of stability in a reaction for a long period of time, and an amount of the target organic compound obtained as the result has not yet met the level of industrial mass production. This results from thermal decomposition of coenzymes required for the enzyme reaction, particularly $NAD^+$ and NADH which are redox coenzymes, not from a problem in stability of an enzyme module used. In order to stably synthesize a target organic compound for a long period of time, it is necessary to appropriately supplement $NAD^+$ and NADH which are reduced due to thermal decomposition, from outside the reaction system, but $NAD^+$ and the like are relatively expensive and this is why there is no progress in industrial use of the method using the artificial metabolic system.

The main purpose of the present invention is to provide a method for synthesizing $NAD^+$ or NADH in an enzyme reaction system in order to supplement $NAD^+$ or NADH lost due to thermal decomposition in the enzyme reaction system requiring $NAD^+$ or NADH, and a transformant set for producing $NAD^+$ or NADH used in the method.

Solution to Problem

As a result of intensive research, the inventors of the present invention have constructed an artificial metabolic pathway for salvage synthesis of $NAD^+$ from nicotinamide which is a thermal decomposition product of $NAD^+$ ($NAD^+$ artificial synthesis pathway) and an artificial metabolic pathway for salvage synthesis of NADH from nicotinamide (NADH artificial synthesis pathway), and have found that an enzyme reaction system requiring $NAD^+$ or NADH can be supplemented with $NAD^+$ or NADH lost due to thermal decomposition more inexpensively by adding metabolic enzymes required for the $NAD^+$ artificial synthesis pathway or for the NADH artificial synthesis pathway to the enzyme reaction system so that $NAD^+$ or NADH is synthesized in the enzyme reaction system, not by externally adding $NAD^+$ or NADH directly, and therefore have completed the present invention.

That is, a method for producing a coenzyme, and a transformant set for coenzyme production according to the present invention are the following [1] to [18].

[1] A method for producing a coenzyme, including performing synthesis of $NAD^+$ in an enzyme reaction system requiring $NAD^+$ by adding one or more thermostable enzymes required for a reaction for synthesizing $NAD^+$ from ADP-ribose and nicotinamide, to the enzyme reaction system.

[2] The method for producing a coenzyme according to [1], in which the thermostable enzymes required for a reaction for synthesizing $NAD^+$ are nicotinamidase, nicotinate phosphoribosyltransferase, nicotinate-nucleotide adenylyltransferase, $NAD^+$ synthase, ADP-ribose pyrophosphatase, and ribose-phosphate pyrophosphokinase.

[3] A method for producing a coenzyme, including performing synthesis of NADH in an enzyme reaction system requiring NADH by adding one or more thermostable enzymes required for a reaction for synthesizing NADH from ADP-ribose and nicotinamide, to the enzyme reaction system.

[4] The method for producing a coenzyme according to [3], in which the thermostable enzymes required for a reaction for synthesizing NADH are nicotinamidase, nicotinate phosphoribosyltransferase, nicotinate-nucleotide adenylyltransferase, $NAD^+$ synthase, ADP-ribose pyrophosphatase, ribose-phosphate pyrophosphokinase, and oxidoreductase that catalyzes a reaction for synthesizing NADH from $NAD^+$.

[5] The method for producing a coenzyme according to [4], in which the oxidoreductase is dehydrogenase with sugar, alcohol, or organic acid as a substrate.

[6] The method for producing a coenzyme according to any one of [1] to [5], further including performing synthesis of ATP in the enzyme reaction system by adding one or more thermostable enzymes required for a reaction for synthesizing ATP from AMP or ADP, to the enzyme reaction system.

[7] The method for producing a coenzyme according to [6], in which the thermostable enzymes required for a reaction for synthesizing ATP are adenylate kinase and polyphosphate kinase.

[8] The method for producing a coenzyme according to any one of [1] to [7], in which the thermostable enzyme is synthesized by an expression system of a non-thermostable microorganism.

[9] The method for producing a coenzyme according to any one of [1] to [8], in which the thermostable enzyme is synthesized by a transformant into which a gene encoding the thermostable enzyme is introduced by using a non-thermostable microorganism as a host.

[10] The method for producing a coenzyme according to [9], in which a heat treated product of microbial cells obtained by culturing the transformant is added to the enzyme reaction system.

[11] The method for producing a coenzyme according to any one of [8] to [10], in which the non-thermostable microorganism is *E. coli*.

[12] A transformant set for coenzyme production, including one or more transformants into which one or more genes encoding thermostable enzymes required for a reaction for synthesizing $NAD^+$ or NADH from ADP-ribose and nicotinamide are introduced by using a non-thermostable microorganism as a host.

[13] The transformant set for coenzyme production according to [12], in which the thermostable enzymes are nicotinamidase, nicotinate phosphoribosyltransferase, nicotinate-nucleotide adenylyltransferase, $NAD^+$ synthase, ADP-ribose pyrophosphatase, and ribose-phosphate pyrophosphokinase.

[14] The transformant set for coenzyme production according to [12], in which the thermostable enzymes are nicotinamidase, nicotinate phosphoribosyltransferase, nicotinate-nucleotide adenylyltransferase, $NAD^+$ synthase, ADP-ribose pyrophosphatase, ribose-phosphate pyrophosphokinase, and oxidoreductase that catalyzes a reaction for synthesizing NADH from $NAD^+$.

[15] The transformant set for coenzyme production according to any one of [12] to [14], further including one or more transformants into which one or more genes encoding thermostable enzymes required for a reaction for synthesizing ATP from AMP or ADP are introduced by using a non-thermostable microorganism as a host.

[16] The transformant set for coenzyme production according to any one of [12] to [15], in which one type of genes encoding the thermostable enzymes is introduced into one transformant.

[17] The transformant set for coenzyme production according to any one of [12] to [16], in which the non-thermostable microorganism is *E. coli*.

[18] The transformant set for coenzyme production according to any one of [12] to [17], in which the transformant is heat treated.

Advantageous Effects of Invention

By using a method for producing a coenzyme according to the present invention, it is possible to stably perform a target enzyme reaction system using an enzyme essentially requiring $NAD^+$ or NADH as a coenzyme, which are likely to be lost due to thermal decomposition, for a long period of time, even without externally adding expensive $NAD^+$ or NADH after the start of the enzyme reaction.

In addition, by using a transformant set for coenzyme production according to the present invention, the method for producing a coenzyme can be carried out more easily.

DESCRIPTION OF EMBODIMENTS

A method for producing a coenzyme according to the present invention includes performing salvage synthesis of NAD$^+$ or NADH in an enzyme reaction system requiring NAD$^+$ or NADH by adding one or more thermostable enzymes required for a reaction for synthesizing NAD$^+$ or NADH from nicotinamide, to the enzyme reaction system. The method for producing a coenzyme according to the present invention may be used for the enzyme reaction system requiring both NAD$^+$ and NADH. Among the methods for producing a coenzyme according to the present invention, a method for performing salvage synthesis of NAD$^+$ by adding one or more thermostable enzymes required for a reaction for synthesizing NAD$^+$, to the enzyme reaction system requiring NAD$^+$ is called "a method for producing NAD$^+$". Among the methods for producing a coenzyme according to the present invention, a method for performing salvage synthesis of NADH by adding one or more thermostable enzymes required for a reaction for synthesizing NADH, to the enzyme reaction system requiring NADH is called "a method for producing NADH". NAD$^+$ or NADH is synthesized from nicotinamide which is a thermal decomposition product of NAD$^+$ or NADH in the enzyme reaction system requiring NAD$^+$ or NADH. This makes it possible to supplement NAD$^+$ or NADH lost due to thermal decomposition in the system, even without externally adding NAD$^+$ or NADH directly and to stably synthesize an organic compound that is a target product of the enzyme reaction system for a long period of time.

In the method for producing NAD$^+$ according to the present invention, "the enzyme reaction system requiring NAD$^+$" means a reaction system that is an extracellular reaction system (so-called in vitro reaction system) and that includes an enzyme reaction by an enzyme requiring NAD$^+$ as a coenzyme. The enzyme reaction system may be a reaction system consisting of only one step enzyme reaction, and may be a reaction system consisting of two or more steps enzyme reaction. In a case of the enzyme reaction system consisting of two or more steps enzyme reaction, at least one step may be the enzyme reaction by the enzyme requiring NAD$^+$ as a coenzyme. In addition, the enzyme requiring NAD$^+$ as a coenzyme is not particularly limited and can be appropriately determined based on a target organic compound and a reaction pathway.

In the method for producing NADH according to the present invention, "the enzyme reaction system requiring NADH" means a reaction system that is an extracellular reaction system (so-called in vitro reaction system) and that includes an enzyme reaction by an enzyme requiring NADH as a coenzyme. The enzyme reaction system may be a reaction system consisting of only one step enzyme reaction, and may be a reaction system consisting of two or more steps enzyme reaction. In a case of the enzyme reaction system consisting of two or more steps enzyme reaction, at least one step may be the enzyme reaction by the enzyme requiring NADH as a coenzyme. In addition, the enzyme requiring NADH as a coenzyme is also not particularly limited and can be appropriately determined based on a target organic compound and a reaction pathway.

In the method for producing a coenzyme according to the present invention, as the enzyme reaction system requiring NAD$^+$ or NADH, a reaction system performed in neutral to alkaline environments is preferable, a reaction system performed in an alkalescent environment in which pH is 7.6 to 9.0 is more preferable, and a reaction system performed in an alkalescent environment in which pH is 7.8 to 8.5 is further more preferable. In a case where pH of the reaction system is neutral to alkaline, main thermal decomposition products of NAD$^+$ or NADH are nicotinamide and ADP-ribose, and this is because NAD$^+$ and NADH can be efficiently resynthesized by the method for producing a coenzyme according to the present invention.

A target organic compound synthesized by the enzyme reaction system requiring NAD$^+$ or NADH is not particularly limited. Organic compounds such as lactic acid, malic acid, n-butanol and the like, which are useful as a raw material for chemically synthesized products, medicines, cosmetics, foods and beverages, are preferable.

In the method for producing NAD$^+$ according to the present invention, "a reaction for synthesizing NAD$^+$ from nicotinamide" means an enzyme reaction in which NAD$^+$ is synthesized last through an enzyme reaction of one or more steps with nicotinamide as a substrate. Hereinafter, the reaction is referred to as a "NAD$^+$ salvage synthesis pathway" in some cases. The NAD$^+$ salvage synthesis pathway may be a natural metabolic pathway inherent in any living organisms, may be a pathway in which the natural metabolic pathway is appropriately modified, and may be a metabolic pathway synthesized artificially.

Figure 1:
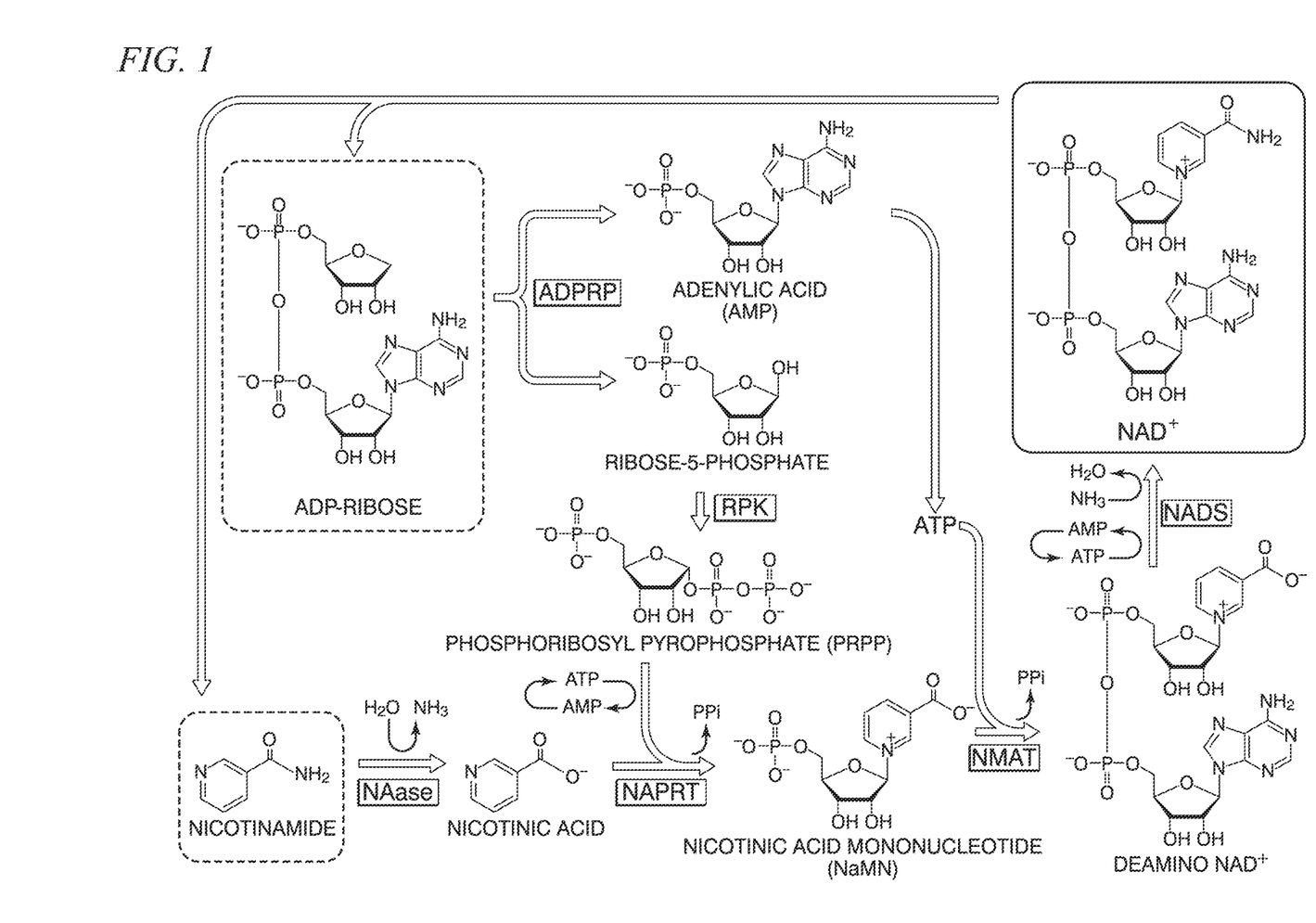
FIG. 1 is a diagram showing an aspect of a $NAD^+$ salvage synthesis pathway having ADP-ribose and nicotinamide as a starting raw material.

Specific examples of the NAD$^+$ salvage synthesis pathway include a pathway having ADP-ribose and nicotinamide as a starting raw material and using a nicotinamidase (NAase), a nicotinate phosphoribosyltransferase (NAPRT), a nicotinate-nucleotide adenylyltransferase (NMAT), a NAD$^+$ synthase (NADS), an ADP-ribose pyrophosphatase (ADPRP), and a ribose-phosphate pyrophosphokinase (RPK), as shown in FIG. 1. Ribose-5-phosphate is synthesized by the ADP-ribose pyrophosphatase with the ADP-ribose as a substrate, and phosphoribosyl pyrophosphate (PRPP) is synthesized by the ribose-phosphate pyrophosphokinase with the ribose-5-phosphate as a substrate. Aside from this, a nicotinic acid is synthesized by the nicotinamidase with the nicotinamide as a substrate. Nicotinic acid mononucleotide (NaMN) is synthesized by the nicotinate phosphoribosyltransferase with a nicotinic acid and phosphoribosyl pyrophosphate as a substrate, and deamino NAD$^+$ is synthesized by nicotinate-nucleotide adenylyltransferase from nicotinic acid mononucleotide and ATP. NAD$^+$ is synthesized by NAD$^+$ synthase with this deamino NAD$^+$ as a substrate.

Figure 2:
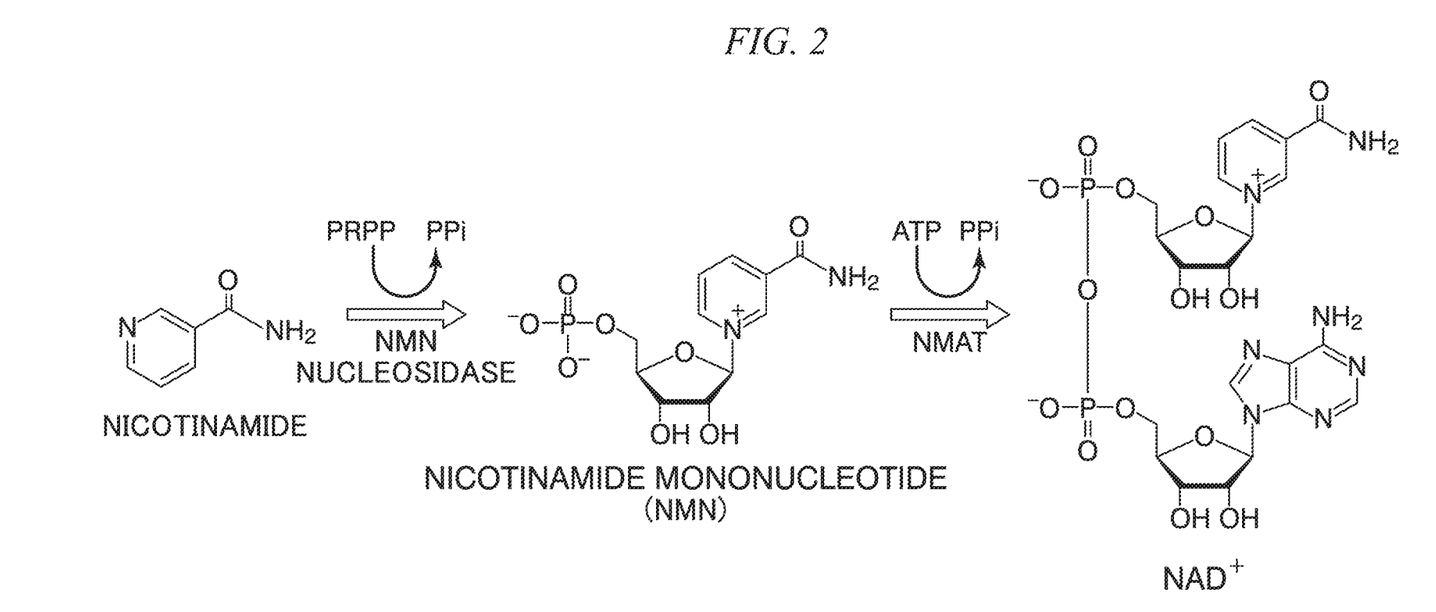
FIG. 2 is a diagram showing an aspect of the $NAD^+$ salvage synthesis pathway having nicotinamide as a starting raw material.

Examples of the NAD$^+$ salvage synthesis pathway include a pathway having nicotinamide as a starting raw material and using a NMN nucleosidase and nicotinate-nucleotide adenylyltransferase, as shown in FIG. 2. Nicotinamide mononucleotide (NMN) is synthesized by a NMN nucleosidase from nicotinamide and a phosphorylated ribose donor such as phosphoribosyl pyrophosphate (PRPP), and NAD$^+$ is synthesized by nicotinate-nucleotide adenylyltransferase with nicotinamide mononucleotide as a substrate.

In the method for producing NADH according to the present invention, "a reaction for synthesizing NADH from nicotinamide" means an enzyme reaction in which NADH is synthesized last through an enzyme reaction of one or more steps with nicotinamide as a substrate. Hereinafter, the reaction is referred to as a "NADH salvage synthesis pathway" in some cases. The NADH salvage synthesis pathway may be a natural metabolic pathway inherent in any living organisms, may be a pathway in which the natural metabolic pathway is appropriately modified, and may be a metabolic pathway synthesized artificially.

NADH is decomposed to NAD$^+$ through thermal decomposition, and then decomposed to ADP-ribose and nicotinamide. As the NADH salvage synthesis pathway, a reaction pathway on which NADH is synthesized from ADP-ribose and nicotinamide is preferable. For example, it is possible to set a pathway in which an oxidoreductase that catalyzes a reaction for synthesizing NADH from NAD$^+$ is added to the NAD$^+$ salvage synthesis pathway, as the NADH salvage synthesis pathway.

The reaction for synthesizing NADH from NAD$^+$ can be performed by various oxidation reactions with NAD$^+$ as the coenzyme. A substrate of the oxidation reactions with NAD$^+$ as the coenzyme and the oxidoreductase are not particularly limited. Examples of the oxidoreductase that catalyzes a reaction for synthesizing NADH from NAD$^+$ and that is used in the present invention can include a dehydrogenase with a sugar, an alcohol, or an organic acid as a substrate. Examples of the dehydrogenase with a sugar as a substrate include a glucose dehydrogenase (EC. 1.1.1.47), a glucose-6-phosphate dehydrogenase (EC. 1.1.1.49), a galactose-1-dehydrogenase (EC. 1.1.1.48), a L-arabinose-1-dehydrogenase (EC. 1.1.1.46), a D-xylose-1-dehydrogenase (EC. 1.1.1.175), a glucuronate reductase (EC. 1.1.1.19), and the like. Examples of the dehydrogenase with an alcohol as a substrate include an alcohol dehydrogenase (EC. 1.1.1.1), a glycerol dehydrogenase (EC. 1.1.1.6), a glycerol-3-phosphate dehydrogenase (NAD$^+$) (EC. 1.1.1.8) a mannitol-1-phosphate-5-dehydrogenase (EC. 1.1.1.17), an inositol-2-dehydrogenase (EC. 1.1.1.18), a mannitol-2-dehydrogenase (EC. 1.1.1.67), and the like. Examples of the dehydrogenase with an organic acid as a substrate include a lactate dehydrogenase (EC. 1.1.1.27 EC. 1.1.1.28), a malate dehydrogenase (EC. 1.1.1.37, EC. 1.1.1.38, EC. 1.1.1.39), an isocitrate dehydrogenase (EC. 1.1.1.41), a tartrate dehydrogenase (EC. 1.1.1.93), a gluconate-5-dehydrogenase (EC. 1.1.1.69), a formate dehydrogenase (EC. 1.2.1.2), and the like.

As the oxidoreductase that catalyzes a reaction for synthesizing NADH from NAD$^+$ and that is used in the present invention, it is particularly preferable to use the glucose dehydrogenase, the formate dehydrogenase, the alcohol dehydrogenase, or the lactate dehydrogenase because a substrate thereof is relatively inexpensive. For example, by adding glucose and glucose dehydrogenase to the enzyme reaction system in which salvage synthesis of NADH is performed, NADH is synthesized together with gluconolactone from salvage-synthesized NAD$^+$ and glucose by glucose dehydrogenase. Similarly, by adding a formic acid and a formate dehydrogenase to the enzyme reaction system in which salvage synthesis of NADH is performed, NADH is synthesized together with carbon dioxide, and by adding an alcohol and an alcohol dehydrogenase, NADH is synthesized together with aldehyde, and by adding a lactic acid and a lactate dehydrogenase, NADH is synthesized together with a pyruvic acid.

In the method for producing a coenzyme according to the present invention, as an enzyme required for the NAD$^+$ salvage synthesis pathway or the NADH salvage synthesis pathway, which is added to the enzyme reaction system requiring NAD$^+$ or NADH, the thermostable enzyme is preferable. Because the thermostable enzyme excels in chemical and thermal stability compared to a non-thermostable enzyme, it is possible to more stably synthesize NAD$^+$ or NADH in the enzyme reaction system.

In the present invention and the specification of the present application, "the thermostable enzyme" means an enzyme that can maintain enzyme activity without denaturation even in a case of being subjected to a heat treatment at 60° C. As the thermostable enzyme added to the enzyme reaction system requiring NAD$^+$, an enzyme that can maintain the enzyme activity and has thermal resistance without denaturation even in a case of being subjected to a heat treatment at 70° C. is preferable.

The thermostable enzyme may be a natural enzyme (enzyme inherent in any living organisms), may be an enzyme in which a natural enzyme is modified, and may be an enzyme designed and synthesized artificially. For example, the natural thermostable enzyme can be isolated from hyperthermophilic microorganisms or thermophilic microorganisms. Examples of the hyperthermophilic microorganisms or the thermophilic microorganisms include microorganisms belonging to *Pyrococcus* such as *Pyrococcus horikoshii, Pyrococcus abyssi, Pyrococcus glycovorans, Pyrococcus furiosus*, and *Pyrococcus wosei*; *Methanopyrus* such as *Methanopyrus kandleri*; *Pyrolobus* such as *Pyrolobus fumarii*; *Sulfolobus* such as *Sulfolobus acidocaldarius, Sulfolobus islandicus, Sulfolobus solfataricus*, and *Sulfolobus tokodaii*; *Pyrodictium* such as *Pyrodictium occultum, Pyrodictium abyssi*, and *Pyrodictium brockii*; *Hyperthermus* such as *Hyperthermus butylicus*; *Pyrobaculum* such as *Pyrobaculum aerophilum, Pyrobaculum arsenaticum*, and *Pyrobaculum organotrophum*; *Aeropyrum* such as *Aeropyrum pernix*; *Thermococcus* such as *Thermococcus profundus, Thermococcus kodakarensis*, and *Thermococcus gammatolerans*; *Aquifex* such as *Aquifex pyrophilus*; *Thermotoga* such as *Thermotoga maritima, Thermotoga naphthophila, Thermotoga lettingae, Thermotoga neapolitana*, and *Thermotoga petrophila*; *Thermodesulfobacterium* such as *Thermodesulfobacterium commune*; *Thermus* such as *Thermus thermophilus* and *Thermus aquaticus*; *Thermoplasma* such as *Thermoplasma acidophilum* and *Thermoplasma volcanium*; *Geobacillus* such as *Geobacillus stearothermophilus*; *Acidilobus* such as *Acidilobus saccharovorans*; *Sulfolobus* such as *Sulfolobus solfataticus*, and the like.

In a case of multistep reaction of the NAD$^+$ salvage synthesis pathway or the NADH salvage synthesis pathway, a rate of enzyme reaction at each step is determined by a reaction rate of the enzyme reaction itself and abundance of the thermostable enzyme in the enzyme reaction system. It is preferable to add a sufficient amount of each of the thermostable enzymes used in these synthesis pathways to the reaction system so that reaction efficiency is not reduced due to lack of enzyme amount. In particular, it is preferable that the thermostable enzyme having a relatively slower reaction rate is added in an amount (unit amount) sufficient for the reaction system so that the enzyme reaction by the thermostable enzyme is not rate-limiting. It is also preferable to add a sufficient amount thereof to the enzyme reaction system so that the amount thereof becomes larger than the abundance of the thermostable enzyme having a relatively faster reaction rate. By adjusting the abundance of the thermostable enzyme in the enzyme reaction system with consideration of a balance with the reaction rate, it is possible to more quickly and efficiently synthesize NAD$^+$ or NADH while suppressing the amount of enzymes. In the method for producing a coenzyme according to the present invention, the thermostable enzyme may be added to the enzyme reaction system before start of the enzyme reaction for synthesizing a target organic compound of the enzyme reaction system, and may be added to the enzyme reaction system after start of the enzyme reaction.

For example, in a case of the NAD$^+$ salvage synthesis pathway shown in FIG. 1, it is preferable to add each of the thermostable enzymes to the enzyme reaction system such that an abundance ratio (unit ratio) of each of the thermostable enzymes present in the enzyme reaction system becomes nicotinate phosphoribosyltransferase=5 to 50, nicotinate-nucleotide adenylyltransferase=10 to 100, NAD$^+$ synthase=200 to 600, ADP-ribose pyrophosphatase=1 to 2, and ribose-phosphate pyrophosphokinase=5 to 10, with respect to nicotinamidase=1, and it is more preferable to add each of the thermostable enzymes to the enzyme reaction system such that the ratio becomes nicotinamidase:nicotinate phosphoribosyltransferase:nicotinate-nucleotide adenylyltransferase:NAD$^+$ synthase:ADP-ribose pyrophosphatase:ribose-phosphate pyrophosphokinase=1:50:75:500: 1.2:10.

Figure 3:
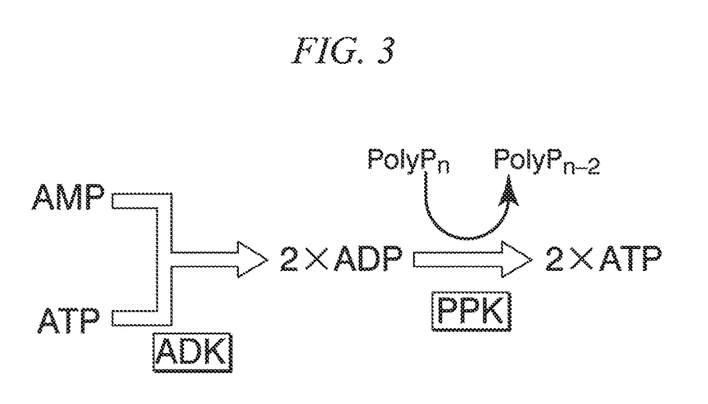
FIG. 3 is a diagram showing an aspect of an ATP synthesis pathway.

In the NAD$^+$ salvage synthesis pathway and the NADH salvage synthesis pathway, the reaction using ATP is included. In the method for producing a coenzyme according to the present invention, in addition to the thermostable enzyme required for the NAD$^+$ salvage synthesis pathway or the NADH salvage synthesis pathway, it is preferable to add the thermostable enzyme required for the reaction of synthesizing ATP (ATP synthesis pathway) to the enzyme reaction system requiring NAD$^+$ or NADH. Specific examples of the ATP synthesis pathway include a pathway having AMP and ATP as a starting raw material and using adenylate kinase (ADK) and polyphosphate kinase (PPK), as shown in FIG. 3. Two molecules of ADP are synthesized by adenylate kinase from one molecule of AMP and one molecule of ATP, and from these two molecules of ADP, two molecules of ATP are synthesized by polyphosphate kinase.

It is possible to produce the thermostable enzyme required for the NAD$^+$ salvage synthesis pathway, the thermostable enzyme required for the NADH salvage synthesis pathway, and the thermostable enzyme required for the ATP synthesis pathway, which are used in the present invention, by an expression system using the metabolic system of microorganisms. The expression system may be an expression system expressed in the transformant in which a gene encoding the thermostable enzyme (thermostable enzyme gene) is introduced into a microorganism, and may be a cell free expression system.

When the thermostable enzyme added to the enzyme reaction system in the present invention is synthesized in the transformant, the thermostable enzyme expressed by one transformant may be one, or may be two or more. In addition, all thermostable enzyme genes required for the NAD$^+$ salvage synthesis pathway or for the NADH salvage synthesis pathway may be expressed in one transformant.

Isolation of the thermostable enzyme gene from the hyperthermophilic bacteria or the thermophilic bacteria can be performed according to a known method in this technical field. Specifically, first, after preparing genomic DNA of the hyperthermophilic microorganisms or of the thermophilic microorganisms, the genomic DNA is cut with an appropriate restriction enzyme and is linked, by using ligase or the like, to a plasmid or a phage, which is cut with the same restriction enzyme or a restriction enzyme that gives a common cleavage end, and thereby a genomic DNA library is prepared. Subsequently, using a primer set designed based on a base sequence of a target thermostable enzyme to be acquired, it is possible to obtain a target thermostable enzyme gene by performing PCR with the genomic DNA library thereof as a template. Alternatively, using a probe designed based on the base sequence, it is also possible to obtain a target thermostable enzyme gene by screening the genomic DNA library thereof. The obtained thermostable enzyme gene may be modified to a codon that is frequently used in a host cell without changing an amino acid sequence of the thermostable enzyme to be coded. The modification of the codon can be performed with known technology of genetic recombination.

The thermostable enzyme gene may be a chimeric gene in which various tags are attached to a N terminal or a C terminal. As the tags, for example, it is possible to use a tag such as His-tag, a HA (hemagglutinin)-tag, a Myc tag, and a Flag-tag, which are generally used in expression or purification of a recombinant protein. With the thermostable enzyme being expressed in a state where a tag is attached thereto, the purification from the expression system and measurement of the amount of expression and the like becomes easy.

The preparation of the transformant in which the thermostable enzyme gene is introduced into a host cell can be performed using a known method or a method in which a known method is modified appropriately. Specifically, for example, there is a method in which a recombinant vector containing the gene is obtained by linking the thermostable enzyme gene to an appropriate vector, and then a host cell is transformed using the recombinant vector. The transformation of the host cell using the recombinant vector can be performed according to a known method such as a calcium chloride method and an electroporation method.

The vector used for introduction of the thermostable enzyme gene is not particularly limited as long as the vector can be obtained by expressing the thermostable enzyme in a host cell to be transformed. For example, it is possible to use a vector such as a plasmid and a phage. Specific examples thereof include pET11a, pET21a, pUC18, pKK223-3, pBAD, pRCI (Ninh et al., Biotechnology and Bioengineering, 2015, vol. 112, p. 189-196), pNit-QT2, pNit-RC2, pTip-QT2, pTip-RC2, and the like. In addition, the recombinant vector preferably contains a promoter or other regulatory sequences (for example, an enhancer sequence and a terminator sequence) for allowing expression of the thermostable enzyme gene in the host cell. Specific examples of the promoter include promoters such as a T7 promoter, a lambda PR promoter, a PnitA promoter, a PtipA promoter, a lac promoter, a tac promoter, and a pBAD/AraC promoter.

In a case where a plurality of the thermostable enzymes are required for the NAD$^+$ salvage synthesis pathway and the NADH salvage synthesis pathway, the promoters regulating the expression of each of the thermostable enzyme genes may be all the same types, or may be different types from each other. In a case where the promoters regulating the expression of each of the thermostable enzyme genes are not all the same types, as a promoter regulating the expression of the thermostable enzyme of having a slow reaction rate and of which an amount of addition to the enzyme reaction system is relatively large, it is preferable to use a promoter having high expression efficiency. As a promoter regulating the expression of the thermostable enzyme of having a fast reaction rate and of which an amount of addition to the enzyme reaction system is relatively small, a promoter having relatively low high expression efficiency may be used.

In addition, a marker gene may be contained in the recombinant vector so that the selection of transformed cells becomes possible. Examples of the marker gene include a gene complementing auxotrophy of a host, a gene resistant to drugs and the like.

The host cell for obtaining the transformant into which the thermostable enzyme gene is introduced is not particularly limited, and may be a prokaryotic cell, may be a eukaryotic single cell, or may be a cell of a eukaryotic multicellular organism. The cell of a eukaryotic multicellular organism may be a plant cell, or may be an animal cell such as an insect cell or a mammalian cell. The host cell is preferably a microorganism because a microorganism is easy to culture and is suitable for large scale expression.

As the host cell for obtaining the transformant into which the thermostable enzyme gene is introduced, a non-thermostable microorganism is particularly preferable. In a case where the thermostable enzyme is expressed in the transformant with the non-thermostable microorganism as the host cell, by heat treating the transformant, all proteins derived from the host cell can be deactivated by thermal denaturation while maintaining the activity of the thermostable enzyme. Therefore, even in a case where the proteins derived from the host cell are inserted into the enzyme reaction system together with the thermostable enzyme, unintended side reactions can be suppressed. As the non-thermostable microorganism as the host cell, *E. coli*; *Bacillus* such as *Bacillus subtilis* and *Bacillus megaterium*; *Pseudomonas* such as *Pseudomonas putida* and *Pseudomonas fluorescense*; *Rhodococcus* such as *Rhodococcus erythropolis* and *Rhodococcus opacus*; *Saccharomyces* such as *Saccharomyces cerevisiae*; *Scizosaccharomyces* such as *Scizosaccharomyces pombe*; *Pichia* such as *Pichia pastoris*, and the like are preferable, and *E. coli* is particularly preferable because of high expression efficiency and easy culturing with a relatively low cost.

The thermostable enzyme added to the enzyme reaction system of the present invention may be purified, may be partially purified, and may not be purified. The purification of the thermostable enzyme from the expression system can be performed with a general method.

Particularly, in a case of synthesizing the thermostable enzyme with the transformant into which the thermostable enzyme gene is introduced by using the non-thermostable microorganism as the host cell, it is possible to add a heat treated product of the transformant by which the thermostable enzyme is expressed, to the enzyme reaction system as it is. Through the heat treatment, while maintaining the activity of the thermostable enzyme, the proteins derived from the host cells are deactivated, so that it is possible to directly add the heat treated product to the enzyme reaction system without purifying the thermostable enzyme without unintended side reactions. In addition, the cellular structure of the transformant, especially the cell membrane and the cell wall are partially destroyed through the heat treatment, which leads to the improvement of the permeability of substances to the inside and the outside of the transformant. In other words, since a substrate and a product of the enzyme reaction can permeate the dead sterilized bodies (the transformant after being subjected to the heat treatment), even in a case where the thermostable enzyme in the heat treated product is retained in the dead sterilized bodies of the transformant, and even in a case of adding the heat treated product to the enzyme reaction system as it is, it is possible to perform the enzyme reaction in the enzyme reaction system by the thermostable enzyme among the heat treated products. Furthermore, components such as ADP-ribose, nicotinamide, NAD$^+$, NADH, ATP, and AMP, which are derived from the host cell and contained in the heat treated product can be used as a raw material for the enzyme reaction in the enzyme reaction system.

The cell wall of *E. coli* is relatively easily destroyed by the heat treatment. Therefore, in a case of a transformant into which the thermostable enzyme gene is introduced by using *E. coli* as the host cell, the thermostable enzyme in the heat treated product is likely to be leaked from the dead sterilized bodies rather than retained in the dead sterilized bodies. In a case of adding the heat treated product to the enzyme reaction system, the thermostable enzyme leaked from the dead sterilized bodies is dispersed in the enzyme reaction system. The efficiency of the enzyme reaction by the thermostable enzyme is high in the case where the thermostable enzyme is dispersed in the enzyme reaction system than the case where the thermostable enzyme is retained in the dead sterilized bodies. Also from the viewpoint of the reaction efficiency in the enzyme reaction system, a non-thermostable microorganism in which the cell wall thereof is likely to be destroyed by the heat treatment like *E. coli*, is preferable as the host cell for expressing the thermostable enzyme used in the present invention, than a non-thermostable microorganism in which the cell wall thereof is unlikely to be destroyed by the heat treatment.

In the method for producing a coenzyme according to the present invention, nicotinamide and/or ADP-ribose which are thermal decomposition products of NAD$^+$ and/or NADH originally added as the coenzyme to the enzyme reaction system can be used as a substrate. Thus, it is possible to synthesize NAD$^+$ or NADH without externally adding nicotinamide or ADP-ribose to the enzyme reaction system. In addition, only NAD$^+$ synthesized by the NAD$^+$ salvage synthesis pathway may be used in the enzyme reaction system, by adding only starting raw materials of the NAD$^+$ salvage synthesis pathway such as nicotinamide to the enzyme reaction system, without adding any NAD$^+$. Similarly; only NADH synthesized by the NADH salvage synthesis pathway may be used in the enzyme reaction system, by adding only starting raw materials of the NADH salvage synthesis pathway such as nicotinamide to the enzyme reaction system, without adding any NADH.

Conditions for the heat treatment of the transformant expressing the thermostable enzyme in the non-thermostable microorganism are not particularly limited as long as the activity of a target thermostable enzyme is maintained and the proteins derived from the host cell are deactivated under the conditions. For example, the heat treatment can be performed under the conditions that the transformant expressing the thermostable enzyme is heated at approximately 60° C. to 90° C. for 1 to 30 minutes.

A transformant set for coenzyme production according to the present invention includes one or more transformants into which one or more gene encoding thermostable enzymes required for the salvage synthesis pathway of the coenzyme are introduced by using a non-thermostable microorganism as a host. Among the transformant sets for coenzyme production according to the present invention, a set including one or more transformants into which one or more genes encoding thermostable enzymes required for the NAD$^+$ salvage synthesis pathway are introduced by using a non-thermostable microorganism as a host, is called a transformant set for NAD$^+$ production. Similarly, a set including one or more transformants into which one or more genes encoding thermostable enzymes required for a NADH salvage synthesis pathway are introduced by using a non-thermostable microorganism as a host, is called a transformant set for NADH production.

The thermostable enzyme required for the NAD$^+$ salvage synthesis pathway is expressed in any of the transformant contained in the transformant set for NAD$^+$ production. In other words, it is possible to produce every type of the thermostable enzyme required for the NAD$^+$ salvage synthesis pathway by culturing the transformant contained in the transformant set for NAD$^+$ production. Similarly, the thermostable enzyme required for the NADH salvage synthesis pathway is expressed in any of the transformant contained in the transformant set for NADH production. By culturing the transformant contained in the transformant set for NADH production, it is possible to produce every type of the thermostable enzyme required for the NADH salvage synthesis pathway.

For example, as shown in FIG. 1, in a case where the NAD⁺ salvage synthesis pathway requires all six types of the thermostable enzymes such as nicotinamidase, nicotinate phosphoribosyltransferase, nicotinate-nucleotide adenylyltransferase, NAD⁺ synthase, ADP-ribose pyrophosphatase, and ribose-phosphate pyrophosphokinase, the transformant set for NAD⁺ production may be consist of one transformant into which all six types of the thermostable enzyme genes are introduced, and may be consist of six types of the transformants in which the thermostable enzyme gene are introduced into each of different transformants. In addition, the set may be consisting of two kinds of the transformants, that are the transformant into which three types among the six types of the thermostable enzyme genes are introduced, and the transformant into which three types of the remainder are introduced.

The transformant set for NAD⁺ production and the transformant set for NADH production may further contain one or more transformants into which one or more genes encoding thermostable enzymes required for the ATP synthesis pathway are introduced.

As the transformant contained in the transformant set for coenzyme production, the transformant described above can be used, and it is preferable transformants obtained by using *E. coli* as the host cell.

The transformant contained in the transformant set for coenzyme production may be in a state of glycerol stock suitable for long term storage, and may be in a state where colonies are formed on an agar medium. In addition, the transformant may be in a state of a culture solution (suspension) cultured to some extent in a culture medium, and may be a transformant in which cultured wet cells are heat treated.

EXAMPLES

Next, the present invention will be described in more detail with examples and the like, but the present invention is not limited by these examples.

<HPLC Analysis>

NAD⁺, ADP-ribose, nicotinamide, nicotinic acid, nicotinic acid mononucleotide, and deamino NAD were subjected to quantitative analysis by HPLC using 5C₁₈ AR-II column (4.6 mm (inner diameter)×250 mm, manufactured by Nacalai Tesque, Inc.). For elution, gradient elution in which a 50 mM potassium phosphate buffer solution (pH 6.5) as eluent A, a solution in which 25% (v/v) methanol and 5 mM sodium 1-octanesulfonate were dissolved in the same buffer solution as eluent B were used. A flow rate of the eluent was set to 0.5 mL/min and the eluent A alone was eluted for 5 minutes from the start of the elution. After increasing a mixing ratio of the eluent B to 0% to 100% (v/v) during 5 to 11 minutes, the eluent B alone was further eluted for 6 minutes. A column temperature was kept at 40° C. and the eluate was monitored at 254 nm.

The quantitative determination of ATP, ADP, and AMP was carried out by HPLC analysis using a HILIC column (4.6 mm (inner diameter)×250 mm, manufactured by Nacalai Tesque, Inc.). As an eluent, a solution in which 20 mM potassium phosphate buffer (pH 7.0) and acetonitrile were mixed in equivalent volume was used and eluted at a flow rate of 1.0 mL/min. The column temperature was kept at 40° C. and the eluate was monitored at 254 nm.

Reference Example 1

Figure 4:
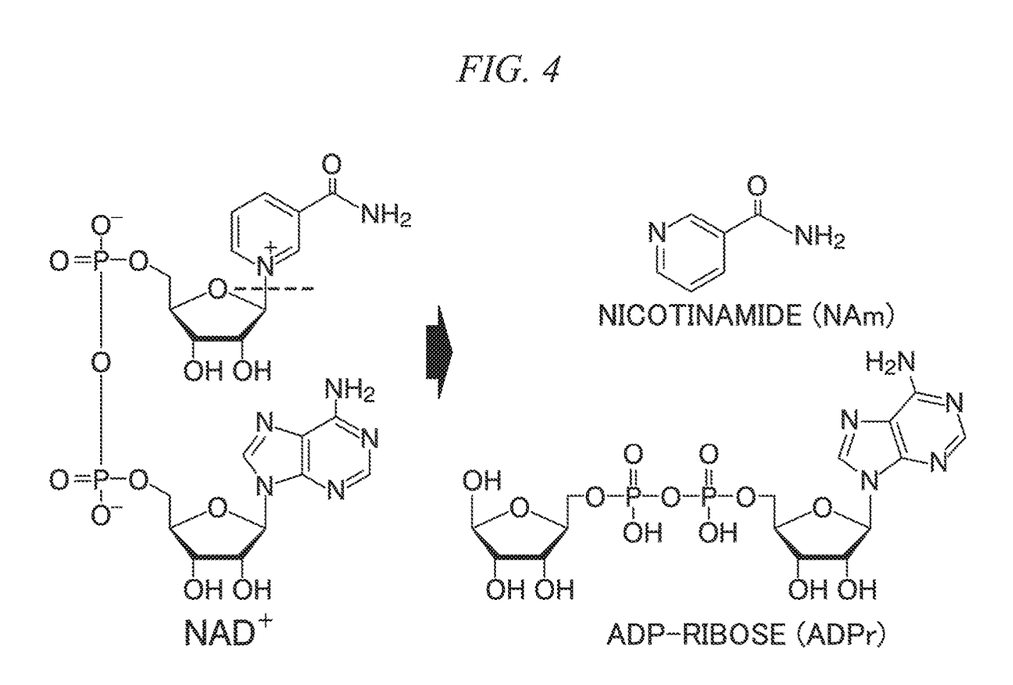
FIG. 4 is a diagram showing a thermal decomposition reaction of $NAD^+$ in Reference Example 1.

When one molecule of NAD⁺ is pyrolysed, one molecule of nicotinamide and one molecule of ADP-ribose are produced (FIG. 4).

Figure 5:
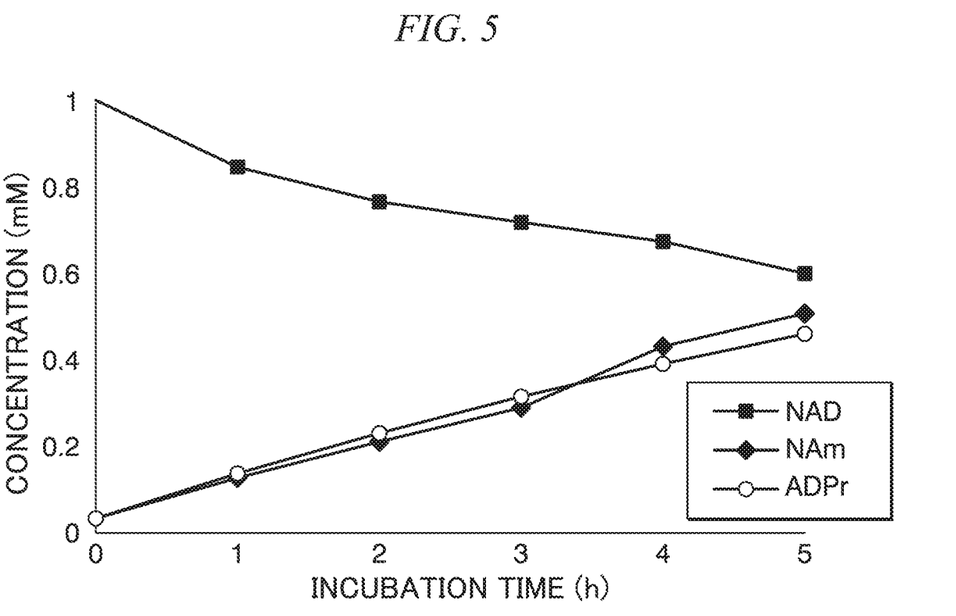
FIG. 5 is a diagram showing a change in $NAD^+$, nicotinamide, and ADP-ribose in the thermal decomposition reaction of $NAD^+$ over time in Reference Example 1.

A NAD⁺ solution with a final concentration of 1 mM was incubated at 70° C. for 3 hours and then subjected to HPLC analysis using a 5C₁₈ AR-II column, and as a result, two peaks were observed in addition to NAD⁺. When compared with the analysis results of various compounds that are composition units of NAD⁺, it became clear that nicotinamide and ADP-ribose showed the same retention time as those peaks. Subsequently, thermal decomposition of NAD⁺ was tracked over time, and it became clear that nicotinamide and ADP-ribose were stoichiometrically accumulated in accordance with decomposition (FIG. 5). These results teach that both substances of nicotinamide and ADP-ribose excelled in thermal stability compared to NAD⁺, and it was determined that both can be used as a starting substance for the salvage synthesis.

The decomposition manner shown here agrees with the findings as an NAD⁺ decomposition scheme under alkaline catalyst proposed in the review by Chenault, et al. (Chenault and Whitesides, Applied Biochemistry and Biotechnology, 1987, vol. 14, p. 147-197).

Example 1

<Design of NAD⁺ Salvage Synthesis Pathway>

The NAD⁺ salvage synthesis pathway with nicotinamide as a starting substance was designed, and two routes shown in FIGS. 1 and 2 were considered. Regarding six types of the enzymes required for the NAD⁺ salvage synthesis pathway shown in FIG. 1, the enzymes shown in Table 1 were selected from the enzymes derived from the hyperthermophilic microorganisms or the thermophilic microorganisms. In addition, regarding two types of the enzymes required for the ATP synthesis pathway and glucose dehydrogenase shown in FIG. 3, the enzymes shown in Table 1 were selected from the enzymes derived from the hyperthermophilic microorganisms or the thermophilic microorganisms. Glucose dehydrogenase is used for the quantitative determination of synthesized NAD⁺. The "GI number" in Table 1 is an accession number of GenBank (base sequence database provided by NCBI (National Center for Biotechnology Information)).

TABLE 1

| Names of enzymes | EC number | Origin | Abbreviation | GI number | Expression vector (promoter) |
|---|---|---|---|---|---|
| Nicotinamidase | 3.5.1.19 | *Thermoplasma acidophilum* | TaNAase | 499203341 | pET21a (T7) |
| Nicotinate phosphoribosyltransferase | 6.3.4.21 | *Thermus thermophilus* HB8 | TtNAPRT | 55980586 | pET11a (T7) |
| Nicotinate-nucleotide adenylyltransferase | 2.7.7.18 | *Thermus thermophilus* HB8 | TtNMAT | 55981749 | pET11a (T7) |

TABLE 1-continued

| Names of enzymes | EC number | Origin | Abbreviation | GI number | Expression vector (promoter) |
|---|---|---|---|---|---|
| NAD+ synthase | 6.3.1.5 | Geobacillus stearothermophilus | GsNADS | 696475119 | pET21a (T7) |
| ADP-ribose pyrophosphatase | 3.6.1.13 | Thermus thermophilus HB8 | TtADPRP | 55771910 | pET11a (T7) |
| Ribose-phosphate pyrophosphokinase | 2.7.6.1 | Thermus thermophilus HB8 | TtRPK | 55981518 | pET11a (T7) |
| Adenylate kinase | 2.7.4.3 | Thermus thermophilus HB8 | TtADK | 55773053 | pET11a (T7) |
| Polyphosphate kinase | 2.7.4.1 | Thermus thermophilus HB27 | TtPPK | 46196569 | pET21a (T7) |
| Glucose dehydrogenase | 1.1.1.118 | Sulfolobus solfataticus | SsGDH | 3786221 | pRCI (lambda PR) |

Nicotinamidase of Thermoplasma acidophilum is an enzyme found as a result of BLAST search using the amino acid sequence of nicotinamidase derived from Acidilobus saccharovorans (GI: 503031789) as a query sequence. Nicotinamidase derived from Acidilobus saccharovorans is reported to have nicotinamidase activity and to be capable of heterologous expression in E. coli. A gene encoding nicotinamidase of Thermoplasma acidophilum is isolated from genomic DNA of Thermoplasma acidophilum by a PCR method. When the isolated enzyme gene was introduced into E. coli and the enzyme was expressed in the obtained transformant, it was confirmed that the enzyme has nicotinamidase activity at 60° C.

In addition, for the amination enzyme (NAD synthase) of deamino NAD+, NAD synthase derived from Thermus thermophilus may be used instead of the enzyme described in Table 1.

TtNMAT in Table 1 is an enzyme that can use not only nicotinic acid mononucleotide (NaMN) but also nicotinamide mononucleotide (NMN) as a substrate.

<Preparation of Transformant>

Regarding the thermostable enzymes described in Table 1, each thermostable enzyme genes were introduced into E. coli to prepare a transformant (recombinant E. coli).

Among the thermostable enzymes described in Table 1, all enzymes derived from Thermus thermophilus HB8 are enzymes included in the single gene expression plasmid library of the same bacterium provided by RIKEN (Yokoyama, et al., Nature Structural Biology, 2000, vol. 7, p. 943-945). An expression vector in the same library is a vector prepared using pET11a (manufactured by Novagen) and a derivative thereof as a backbone. A target gene is placed under the control of the T7 promoter and is induced to be expressed by IPTG Regarding polyphosphate kinase (TtPKK) derived from Thermus thermophilus HB27, and nicotinamidase (TaNAase) derived from Thermoplasma acidophilum, the genes amplified by PCR from genomic DNA of each microorganism were linked to pET21a and were expressed under the control of the T7 promoter in the same manner.

All gene expression vectors were introduced into E. coli Rosetta2 (DE3) pLysS (manufactured by Novagen), and thereby the transformant was prepared.

Glucose dehydrogenase (SsGDH) gene derived from Sulfolobus solfataticus was linked under the control of the lambda PR promoter of pRCI, was introduced into E. coli DH5a strain, and thereby the transformant was prepared.

The expression of the SsGDH genes was induced by shifting a culture temperature to 42° C.

The recombinant E. coli were all cultured aerobically at 37° C. using Luria-Bertani medium containing 100 μg/mL ampicillin. When culturing E. coli Rosetta 2 (DE3) pLysS, 30 μg/mL of chloramphenicol was further added to the medium. Induction of expression of a target enzyme gene was performed by adding 0.2 mM IPTG to a culture solution in a late stage of the logarithmic growth phase, or by heat induction (at 42° C.).

<Preparation of Crude Enzyme Solution>

The wet cells of the recombinant E. coli in which the target thermostable enzyme was expressed were suspended so as to become 200 mg/mL in 100 mM HEPES-NaOH (pH 7.0). The obtained suspension was subjected to ultrasonic disruption treatment to disrupt the wet cells to obtain a cell-free extract. The cell-free extract was subjected to the heat treatment at 70° C. for 30 minutes, and the proteins derived from the host were modified to be deactivated. The heat treated suspension was centrifuged, and the supernatant from which cellular residues and the modified proteins were removed was used as a crude enzyme solution for activity measurement.

<Measurement of Enzyme Activity>

For activity measurement, 400 mM HEPES-NaOH (pH 8.0) was used, and all reactions were carried out at 60° C. The activity of each enzyme was measured as follows. NAD+ generated by being coupled with an enzyme located downstream of the NAD+ salvage synthesis pathway shown in FIG. 1 was further reduced with SsGDH, and then the concentration of accumulated NADH was monitored for absorbance at 340 nm. The activity of enzymes is shown by defining an amount that catalyzes 1 μmol of substrate consumption per minute under this measurement condition as 1 unit (U).

The activity measurement of TaNAase was carried out in a reaction solution consisting of 400 mM HEPES-NaOH (pH 8.0), 1 mM glucose, 60 mM $NH_4Cl_2$, 10 mM $MgCl_2$, 3 mM ATP, 1 mM polyphosphoric acid (average chain length of 60), and 0.2 mM phosphoribosyl pyrophosphate (PRPP). A crude enzyme solution of TaNAase, TtNAPRT, TtNMAT, GsNADS, and SsGDH was added to the reaction solution and preincubated at 60° C. for 3 minutes. At this time, an excessive amount of TtNAPRT, TtNMAT, GsNADS, and SsGDH with respect to an activity value of TaNAase was added such that the reaction of the downstream enzyme is not in the rate-limiting step for the NADH synthesis reaction. After preincubation, nicotinamide at a final concentration of 0.2 mM was added and the increase in absorbance at 340 nm was monitored. For calculation of the reaction rate, a molar absorbance coefficient 6.2 mM$^{-1}$ cm$^{-1}$ of NADH at the same wavelength was used.

Similarly, the activity measurement of TtNAPRT was carried out in the reaction solution of the same composition except that TaNAase was not added. After preincubation, the reaction started by adding 0.2 mM of nicotinic acid as a substrate. Similarly, the activity measurement of TtNMAT and GsNADS was carried out using 0.2 mM of the substrate (nicotinic acid mononucleotide (NaMN), deamino NAD) of each enzyme. In addition, the activity of TtADPRP and TtRPK were measured by quantitatively determining a coupling reaction rate with respect to TtNAPRT, TtNMAT, GsNADS, and SsGDH using 0.2 mM of ADP-ribose and ribose-5-phosphate for each as a substrate.

In addition, in a case of evaluating the activity of each enzyme in the presence of NAD$^+$, each enzyme and the substrate thereof was incubated in 400 mM HEPES-NaOH (pH 8.0) at 60° C., and the concentration of a product was measured by HPLC.

Regarding TtADK and TtPPK, the crude enzyme solution thereof was incubated in 400 mM HEPES-NaOH (pH 8.0) at 60° C. together with 10 mM MgCi$_2$, 0.2 mM ATP, 3.0 mM AMP, and 1 mM polyphosphoric acid, and the ATP accumulation amount and the AMP decrease amount were measured by HPLC.

<Experiment of NAD$^+$ Salvage Synthesis>

The experiment of NAD$^+$ salvage synthesis was carried out in a reaction solution consisting of 400 mM HEPES-NaOH (pH 8.0), 60 mM NH$_4$Cl$_2$, 10 mM MgCl$_2$, 4 mM NAD$^+$, 3 mM ATP, 1 mM polyphosphoric acid (average chain length of 60), 0.2 mM ADP-ribose, and 0.2 mM nicotinamide.

Each crude enzyme solution prepared from the recombinant E. coli in which TaNAase, TtNAPRT, TtNMAT, GsNADS, TtADPRP, TtRPK, TtADK, and TtPPK are separately expressed was added to be mixed in 0.5 mL of the reaction solution such that a final concentration of enzyme becomes 0.02, 0.18, 0.25, 0.51, 0.02, 0.03, 0.05, and 0.05 U/mL, respectively. In addition, as a control experiment, a reaction solution containing neither the recombinant E. coli nor the crude enzyme solution was prepared and incubated at 60° C. Sampling was carried out over time and NAD$^+$ in the reaction solution was quantitatively determined by HPLC.

When 4 mM of NAD$^+$ was incubated in HEPES-NaOH (400 mM, pH 8) at 60° C., a decomposition rate thereof was estimated to be approximately 50 μM/min. By adjusting the addition amount of each enzyme while monitoring the NADH production rate in accordance with the change in absorbance under the reaction condition shown in the measurement method of the enzyme activity, the concentration of the enzyme required for synthesizing NADH from 0.2 mM of each ADP-ribose and nicotinamide at a rate of 50 μM/min was estimated.

Figure 6:
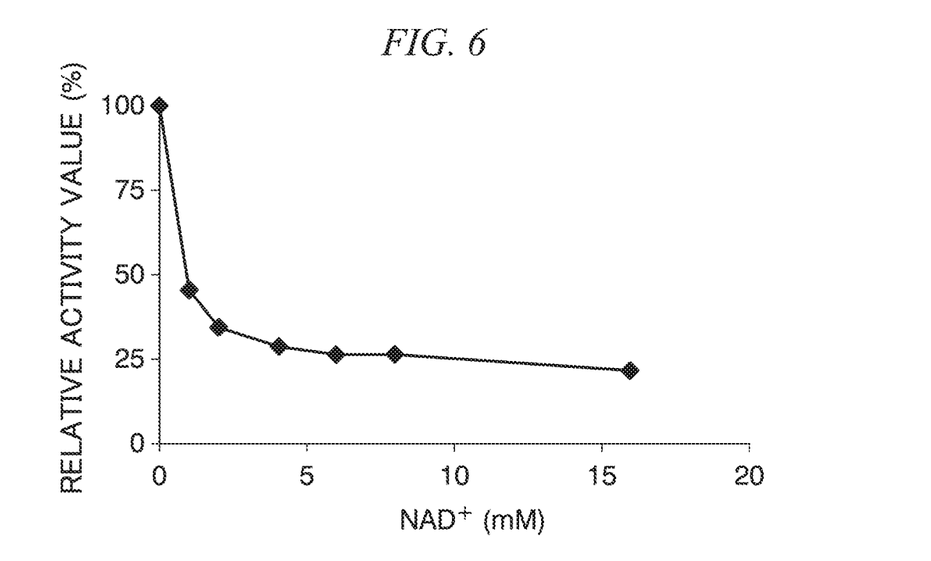
FIG. 6 is a diagram showing an activity value of TtNAPRT (a relative activity value in a case where the activity in a reaction solution not containing $NAD^+$ is set as 100%) under the presence of $NAD^+$ having a concentration shown in a horizontal axis in Example 1.

On the other hand, the activity measurement of each enzyme under the presence of 4 mM NAD$^+$ was carried out by HPLC analysis. As a result, it became clear that TtNAPRT that catalyzes phosphoribosylation of nicotinic acid is significantly inhibited by NAD$^+$. TtNAPRT was incubated in 400 mM HEPES-NaOH (pH 8.0) containing NAD$^+$ having a concentration shown in a horizontal axis in FIG. 6 at 60° C. together with 0.2 mM of each PRPP, ATP, and nicotinic acid, and then a concentration of nicotinic acid mononucleotide (NaMN) in the reaction solution was quantitatively determined by HPLC. The results obtained by calculating an activity value of TtNAPRT (a relative activity value in a case where the activity in the reaction solution not containing NAD$^+$ is set as 100%) are shown in FIG. 6. Under the same conditions, the activity of TtNAPRT was estimated to be approximately ¼ of the activity under the non-presence of NAD$^+$, and therefore it was determined to add this enzyme by an amount of four times the enzyme concentration determined based on the absorbance measurement.

<Coupling with ATP Synthesis Pathway>

In the NAD$^+$ salvage synthesis pathway of FIG. 1, three molecules of ATP are consumed for synthesizing one molecule of NAD$^+$, and three molecules of AMP are released. The ATP synthesis pathway by TtADK and TtPPK from AMP with polyphosphoric acid as phosphate group source was coupled to the NAD salvage synthesis pathway. An amount of enzyme at this case was set to become an excessive amount with respect to a required rate estimated from NAD$^+$ decomposition rate (150 μM/min).

Figure 7:
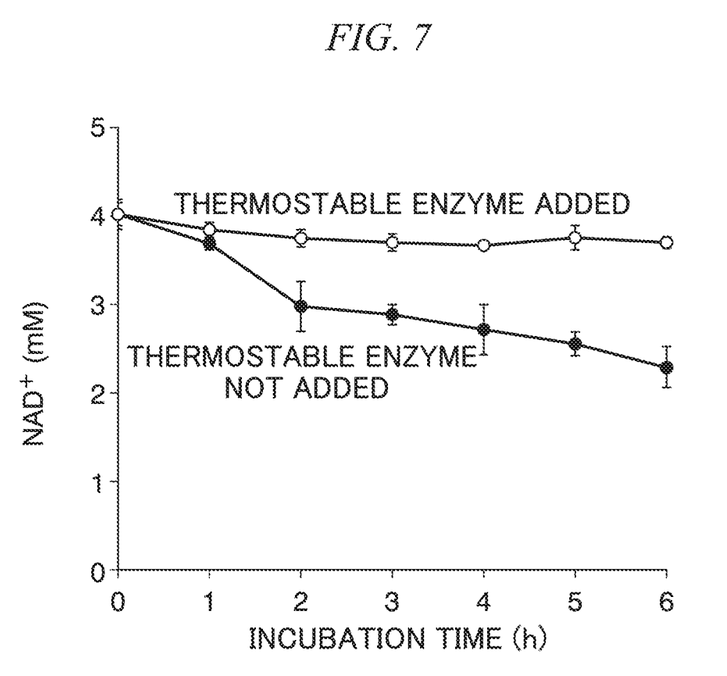
FIG. 7 is a diagram showing a change in a concentration of $NAD^+$ in a reaction solution over time in a case where the reaction solution containing $NAD^+$ and thermostable enzymes required for the $NAD^+$ salvage synthesis pathway and the ATP synthesis pathway is incubated at 60° C. in Example 1.

The crude enzyme solution having the activity value of the concentration determined as above, or the suspension of the recombinant E. coli containing the thermostable enzyme which has the same enzyme activity value as that of the crude enzyme solution was heat treated (at 70° C. for 30 minutes) and added to the reaction solution. In the reaction solution, 4 mM NAD$^+$ was incubated at 60° C. and the change in the concentration thereof was tracked over time (FIG. 7). As a result, it was confirmed that up to at least six hours, the decomposition rate of NAD$^+$ was apparently significantly decreased compared to the case of not adding the enzyme and a concentration of NAD$^+$ close to an initial concentration was continuously maintained. That is, it was confirmed that NAD$^+$ is resynthesized from thermal decomposition products of NAD$^+$ by adding the thermostable enzyme required for the NAD$^+$ salvage synthesis pathway and the ATP synthesis pathway, which results in no apparent decrease in the NAD$^+$ concentration of the system, and therefore it was confirmed that by adding the thermostable enzyme required for the NAD$^+$ salvage synthesis pathway to the enzyme reaction system requiring NAD$^+$, it is possible to suppress the decrease in the concentration of NAD$^+$ caused by the thermal decomposition even without externally adding NAD$^+$, and furthermore, it is possible to stably perform the synthesis of a target organic compound for a long period of time.

Example 2

The experiment of NAD$^+$ salvage synthesis was carried out using the thermostable enzyme required for the NAD$^+$ salvage synthesis pathway and the ATP synthesis pathway. As various thermostable enzymes used, the enzymes used in Example 1 were used.

Specifically, the NAD$^+$ salvage synthesis reaction was carried out in 2 mL of the reaction solution containing 300 mM HEPES-NaOH (pH 8.0), 60 mM NH$_4$Cl$_2$, 10 mM MgCl$_2$, 1 mM polyphosphoric acid (average chain length of 60), 4 mM NAD$^+$, 3 mM ATP, 0.2 mM nicotinamide, 0.2 mM ADP-ribose, and an enzyme cocktail which is a mixture of various thermostable enzymes used in Example 1. Regarding a final concentration of the thermostable enzyme contained in the reaction solution, TaNAase was 0.12 U (0.6 U/mL), TtNAPRT was 0.26 U (0.13 U/mL), TtNMAT was 1.6 U (0.8 U/mL), GsNADS was 10 U (5 U/mL), TtADPRP was 0.12 U (0.6 U/mL), TtRPK was 0.2 U (0.1 U/mL), TtADK was 18 U (9 U/mL), and TtPPK was 10 U (5 U/mL).

Figure 8:
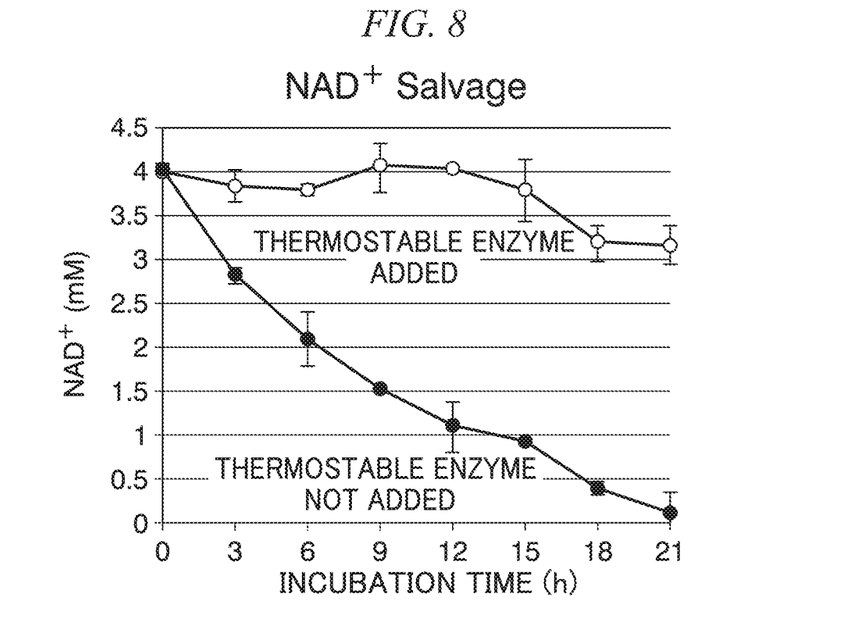
FIG. 8 is a diagram showing a change in a concentration of $NAD^+$ in a reaction solution over time in a case where the reaction solution containing $NAD^+$ and thermostable enzymes required for the $NAD^+$ salvage synthesis pathway and the ATP synthesis pathway is incubated at 60° C. in Example 2.

The reaction solution prepared was incubated at 60° C. In addition, as a control experiment, a reaction solution not containing the enzyme cocktail was prepared and incubated at 60° C. in the same manner. Sampling was carried out for every 3 hours from the start of the reaction, and $NAD^+$ in the reaction solution was quantitatively determined by HPLC. The change in the amount of $NAD^+$ in the reaction solution over time is shown in FIG. 8. In the drawing, "enzyme present" shows the result of the reaction solution added with the enzyme cocktail and "no enzyme" shows the result of the reaction solution with no enzyme cocktail added. As shown in FIG. 8, $NAD^+$ was gradually decreased from immediately after the start of the incubation as the time passes in the reaction solution with no thermostable enzyme added. On the other hand, the amount of $NAD^+$ was not decreased much up to about 21 hours from the start of the incubation in the reaction solution added with the thermostable enzyme required for the $NAD^+$ salvage synthesis pathway and the ATP synthesis pathway. It was confirmed from these results that in the reaction solution, $NAD^+$ was synthesized from decomposition products of $NAD^+$ by the $NAD^+$ salvage synthesis reaction, and the system was also supplemented with ATP required for the $NAD^+$ synthesis by the ATP synthesis reaction.

Example 3

The experiment of NADH synthesis was carried out using the thermostable enzyme required for the NADH salvage synthesis pathway and the ATP synthesis pathway. As various thermostable enzymes used, the enzymes used in Example 1 were used.

Specifically, the NADH salvage synthesis reaction was carried out in 2 mL of the reaction solution containing 300 mM HEPES-NaOH (pH 8.0), 60 mM $NH_4Cl_2$, 10 mM $MgCl_2$, 1 mM polyphosphoric acid (average chain length of 60), 4 mM NADH, 50 mM glucose, 3 mM ATP, 0.2 mM nicotinamide, 0.2 mM ADP-ribose, and an enzyme cocktail which is a mixture of various thermostable enzymes used in Example 1. Regarding a final concentration of the thermostable enzyme contained in the reaction solution, TaNAase was 0.12 U (0.6 U/mL), TtNAPRT was 0.26 U (0.13 U/mL), TtNMAT was 1.6 U (0.8 U/mL), GsNADS was 10 U (5 U/mL), TtADPRP was 0.12 U (0.6 U/mL), TtRPK was 0.2 U (0.1 U/mL), TtADK was 18 U (9 U/mL), TtPPK was 10 U (5 U/mL), and SsGDH was 10 U (5 U/mL).

Figure 9:
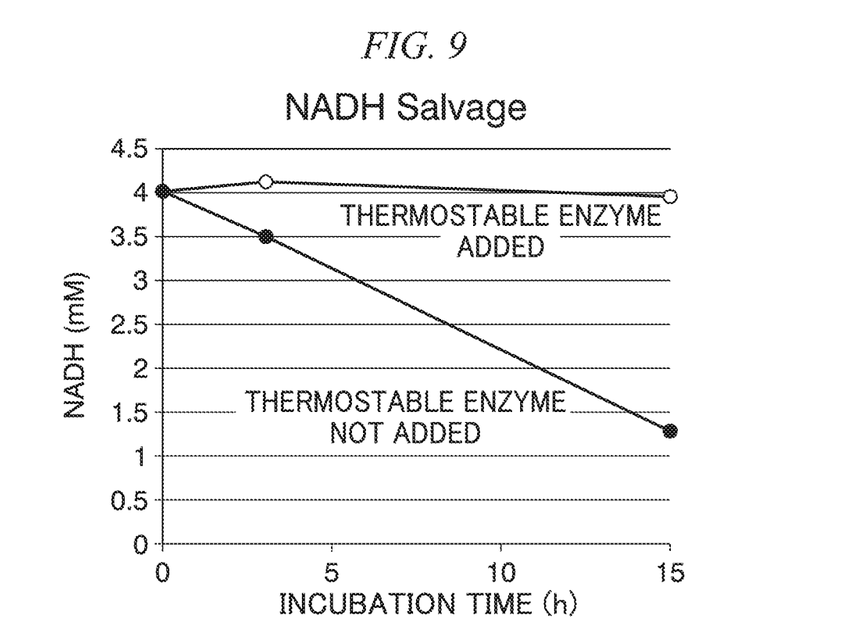
FIG. 9 is a diagram showing a change in a concentration of NADH in a reaction solution over time in a case where the reaction solution containing NADH and thermostable enzymes required for the NADH salvage synthesis pathway and the ATP synthesis pathway is incubated at 60° C. in Example 3.

The reaction solution prepared was incubated at 60° C. In addition, as a control experiment, a reaction solution not containing the enzyme cocktail was prepared and incubated at 60° C. in the same manner. Sampling was carried out for every 3 hours from the start of the reaction, and NADH in the reaction solution was quantitatively determined by HPLC. The change in the amount of NADH in the reaction solution over time is shown in FIG. 9. In the drawing, "enzyme present" shows the result of the reaction solution added with the enzyme cocktail and "no enzyme" shows the result of the reaction solution with no enzyme cocktail added. As shown in FIG. 9, NADH was gradually decreased from immediately after the start of the incubation as the time passes in the reaction solution with no thermostable enzyme added. On the other hand, the amount of NADH was hardly decreased up to about 15 hours from the start of the incubation in the reaction solution added with the thermostable enzyme required for the NADH salvage synthesis pathway and the ATP synthesis pathway. It was confirmed from these results that in the reaction solution, NADH was synthesized from a decomposition product of NADH by the NADH salvage synthesis reaction, and the system was also supplemented with ATP required for the NADH synthesis by the ATP synthesis reaction.

The invention claimed is:

1. A method for producing $NAD^+$ in an extracellular reaction system, the method comprising:
    adding six thermostable enzymes to a mixture of ADP-ribose and nicotinamide, thereby producing $NAD^+$, wherein the six thermostable enzymes are
    nicotinamidase from *Thermoplasma acidophilum*,
    nicotinate phosphoribosyltransferase from *Thermus thermophilus*,
    nicotinate-nucleotide adenylyltransferase from *Thermus thermophilus*,
    NAD+ synthase from *Geobacillus stearothermophilus*,
    ADP-ribose pyrophosphatase from *Thermus thermophilus*, and
    ribose-phosphate pyrophosphokinase from *Thermus thermophilus*.

2. The method according to claim 1, further comprising:
    adding adenylate kinase, AMP, and ATP to the mixture of ADP-ribose and nicotinamide thereby producing ADP.

3. The method according to claim 1 wherein prior to the adding, the method further comprises:
    isolating at least one of the six thermostable enzymes from one or more non-thermostable microorganisms expressing the at least one of the six thermostable enzymes.

4. The method according to claim 3,
    wherein the isolating comprises heat treating the transformant and collecting the thermostable enzyme produced by the transformant.

5. The method according to claim 3, wherein at least one of the one or more non-thermostable microorganisms is *E. coli*.

6. The method according to claim 1, further comprising:
    adding polyphosphate kinase to the mixture, thereby producing ATP.

7. The method according to claim 3, wherein all six thermostable enzymes are isolated from the non-thermostable microorganism.

* * * * *